US009501918B2

(12) United States Patent
Gouge et al.

(10) Patent No.: US 9,501,918 B2
(45) Date of Patent: Nov. 22, 2016

(54) HUMAN SAFETY INDICATOR (75) Inventors: Charles Mack Gouge, Columbus, GA (US); Darrel Self, Davidson, NC (US)

(73) Assignee: Safetyminded Holdings, Inc., Columbus, GA (US)

( * ) Notice: Subject to any disclaimer, the term of this patent is extended or adjusted under 35 U.S.C. 154(b) by 27 days.

(21) Appl. No.: 13/590,609

(22) Filed: Aug. 21, 2012

(65) Prior Publication Data

US 2013/0222138 A1    Aug. 29, 2013

Related U.S. Application Data (60) Provisional application No. 61/526,937, filed on Aug. 24, 2011.

(51) Int. Cl.
| | |
|---|---|
| G08B 23/00 | (2006.01) |
| G08B 21/02 | (2006.01) |
| A61B 5/01 | (2006.01) |
| G01K 13/00 | (2006.01) |
| A61B 5/0205 | (2006.01) |
| A61B 5/00 | (2006.01) |
| A61B 5/11 | (2006.01) |

(52) U.S. Cl.
CPC ............... *G08B 21/02* (2013.01); *A61B 5/01* (2013.01); *A61B 5/02055* (2013.01); *A61B 5/6801* (2013.01); *A61B 5/746* (2013.01); *G01K 13/002* (2013.01); *A61B 5/1118* (2013.01); *A61B 5/681* (2013.01); *A61B 5/6803* (2013.01); *A61B 5/7405* (2013.01); *A61B 5/7455* (2013.01); *A61B 5/7475* (2013.01); *A61B 2560/0431* (2013.01)

(58) Field of Classification Search
None
See application file for complete search history.

(56) References Cited

U.S. PATENT DOCUMENTS

| | | | |
|---|---|---|---|
| 3,678,751 A | 7/1972 | Mead et al. | |
| 4,151,831 A | 5/1979 | Lester | |
| 5,020,547 A | 6/1991 | Strock | |
| 5,235,217 A * | 8/1993 | Kirton | 307/326 |
| 5,441,476 A | 8/1995 | Kitado et al. | |
| 5,486,200 A | 1/1996 | Lindemans | |
| 6,426,719 B1 * | 7/2002 | Nagareda et al. | 342/357.52 |
| 6,615,706 B1 | 9/2003 | Wu | |
| 6,891,136 B2 | 5/2005 | Bikovsky et al. | |

(Continued)

FOREIGN PATENT DOCUMENTS

| | | |
|---|---|---|
| EP | 1081479 | 3/2001 |
| JP | 2006070783 | 3/2006 |

(Continued)

OTHER PUBLICATIONS

Embedded Data Systems, OW-TEMP-xF-12x-Foil Tape Temperature Sensor.*

(Continued)

*Primary Examiner* — Brian Zimmerman
*Assistant Examiner* — Kevin Lau
(74) *Attorney, Agent, or Firm* — Taylor English Duma LLP (57) ABSTRACT A human safety system includes a circuit including at least one power source; a temperature probe in communication with the circuit; at least one use detector in communication with the circuit; and an alert indicator in communication with the circuit. A method of measuring a temperature of a user includes determining whether at least one use detector is active; determining a user temperature based on sensed temperature; and determining whether the user temperature is within an allowable range.

22 Claims, 10 Drawing Sheets (56) References Cited

U.S. PATENT DOCUMENTS

| | | | |
|---|---|---|---|
| 7,087,075 | B2 | 8/2006 | Briscoe et al. |
| 7,329,843 | B2 | 2/2008 | Bikhovsky et al. |
| 7,916,036 | B1 | 3/2011 | Pope et al. |
| 8,175,672 | B2 | 5/2012 | Parker |
| 9,183,719 | B2 | 11/2015 | Gouge et al. |
| 2001/0029325 | A1 | 10/2001 | Parker |
| 2002/0061049 | A1 | 5/2002 | Adachi et al. |
| 2003/0167034 | A1* | 9/2003 | Balding ............... 604/66 |
| 2004/0004547 | A1* | 1/2004 | Appelt et al. ............ 340/573.1 |
| 2004/0026409 | A1 | 2/2004 | Bikhovsky |
| 2004/0064169 | A1 | 4/2004 | Briscoe et al. |
| 2004/0064171 | A1 | 4/2004 | Briscoe et al. |
| 2004/0116822 | A1* | 6/2004 | Lindsey ............... G01K 1/024 600/549 |
| 2004/0122337 | A1 | 6/2004 | Nostro |
| 2004/0188185 | A1* | 9/2004 | Pieper ............... 187/391 |
| 2005/0278069 | A1 | 12/2005 | Bash et al. |
| 2006/0024852 | A1 | 2/2006 | Joshi et al. |
| 2006/0045167 | A1 | 3/2006 | Pawlenko et al. |
| 2006/0206177 | A1 | 9/2006 | Bikhovsky et al. |
| 2007/0150006 | A1 | 6/2007 | Libbus et al. |
| 2007/0239038 | A1 | 10/2007 | Nicolaescu et al. |
| 2007/0294233 | A1* | 12/2007 | Sheu et al. ............... 707/3 |
| 2008/0009691 | A1 | 1/2008 | Parker |
| 2008/0294126 | A1 | 11/2008 | Reuben |
| 2009/0112078 | A1* | 4/2009 | Tabe ............... A61B 5/02055 600/388 |
| 2009/0131165 | A1 | 5/2009 | Buchner et al. |
| 2009/0227924 | A1 | 9/2009 | Conrad et al. |
| 2010/0219956 | A1 | 9/2010 | Greco et al. |
| 2010/0283616 | A1* | 11/2010 | Ruhs et al. ............... 340/573.1 |
| 2011/0023874 | A1 | 2/2011 | Bath et al. |
| 2011/0026562 | A1* | 2/2011 | Bernier et al. ............... 374/184 |
| 2011/0071482 | A1 | 3/2011 | Selevan |
| 2011/0270368 | A1 | 11/2011 | Ginsburg et al. |
| 2012/0036623 | A1 | 2/2012 | Minogue |
| 2012/0048951 | A1 | 3/2012 | Kim et al. |
| 2012/0240918 | A1 | 9/2012 | Kirsch et al. |
| 2012/0293898 | A1 | 11/2012 | Chiang et al. |
| 2013/0005243 | A1* | 1/2013 | Royston ............... 455/41.1 |
| 2013/0234823 | A1 | 9/2013 | Kahn et al. |

FOREIGN PATENT DOCUMENTS

| | | |
|---|---|---|
| JP | 2007260365 | 10/2007 |
| WO | 9731249 | 8/1997 |
| WO | 02084240 | 10/2002 |
| WO | 2008156470 | 12/2008 |

OTHER PUBLICATIONS

Gouge, Charles; U.S. Provisional Patent Application entitled: Human Safey Indicator, having U.S. Appl. No. 61/526,937, filed Aug. 24, 2011, 24 pgs.

Gouge, Charles; U.S. Patent Application entitled: Human Safey Indicator, having U.S. Appl. No. 13/594,300, filed Aug. 24, 2012, 51 pgs.

Gouge, Charles Mack; Non-Final Office Action for U.S. Appl. No. 13/594,300, filed Aug. 24, 2012, mailed Jan. 27, 2014, 23 pgs.

Gouge, Charles Mack; Final Office Action for U.S. Appl. No. 13/594,300, filed Aug. 24, 2012, mailed May 22, 2014, 26 pgs.

Gouge, Charles Mack; Non-Final Office Action for U.S. Appl. No. 13/594,300, filed Aug. 24, 2012, mailed Mar. 13, 2015, 32 pgs.

Gouge, Charles Mack; Advisory Action for U.S. Appl. No. 13/594,300, filed Aug. 24, 2012, mailed Aug. 12, 2014, 5 pgs.

Gouge, Charles Mack; Notice of Allowance for U.S. Appl. No. 13/594,300, filed Aug. 24, 2012, mailed Jul. 6, 2015, 16 pgs.

Gouge, Charles Mack; Issue Notification for U.S. Appl. No. 13/594,300, filed Aug. 24, 2012, mailed Oct. 21, 2015, 1 39.

\* cited by examiner

HUMAN SAFETY INDICATOR

CROSS-REFERENCE TO RELATED APPLICATIONS

This application claims the benefit of U.S. Provisional Application 61/526,937 filed on Aug. 24, 2011, which is hereby incorporated herein in its entirety by reference.

FIELD

The present disclosure relates to temperature safety. More specifically, this disclosure relates to measuring and alerting human temperature.

BACKGROUND

Unsafe temperatures can lead to injury and even death in humans. Athletes, utility workers, construction workers, and manufacturing workers are among those especially subjected to harsh temperatures, increasing the concerns for employers and schools on how to protect workers and athletes. Individuals also may be subjected to dangerous overheating in some circumstances.

SUMMARY

A human safety indicator is disclosed for measuring and alerting a user of his or her susceptibility to temperature. A system, a method, and a device are capable of measuring a user's temperature and alerting the user when the temperature has reached a critical threshold. Other human health factors may be monitored in various embodiments.

DESCRIPTION OF THE FIGURES

The features and components of the following figures are illustrated to emphasize the general principles of the present disclosure and are not necessarily drawn to scale. Corresponding features and components throughout the figures may be designated by matching reference characters for the sake of consistency and clarity.

DETAILED DESCRIPTION

In 2001, an NFL player died of heat stroke after a team practice. Between July and August, 2011, two high school football players in Georgia died from overheating. As illustrated by the two examples above, the problem of overheating has posed for years—and still poses—a grave threat to even the most well-conditioned athletes. Although a decade passed since the NFL player's death, no technology solution existed to prevent the overheating of the Georgia athletes. Utility workers, construction workers, and manufacturing and warehouse employees are also commonly exposed to risks associated with overheating. For many such workers, solutions available to athletes—such as changing practice locations to an air conditioned facility—simply are not available.

Moreover, individuals seeking to train outdoors are often exposed to the risk of heat-related injuries. Joggers, cross-trainers, cyclists, and even gardeners who spend prolonged amounts of time in hot outdoor weather are at risk for severe injury. Although an advanced heat safety system may be possible for certain workers and team athletes, individuals lack funds for such advanced systems.

Additionally, some systems monitor athletes and report data to a central location. However, the cost of such infrastructure is generally too high for small-scale use. Moreover, when errors occur with such systems, potential legal liability is placed on the monitoring party. For example, when a school adopts a system to monitor athletes' health during outdoor activity, a failure in that monitoring system could expose the school to liability for injuries occurring as a result of such failure.

Figure 1:
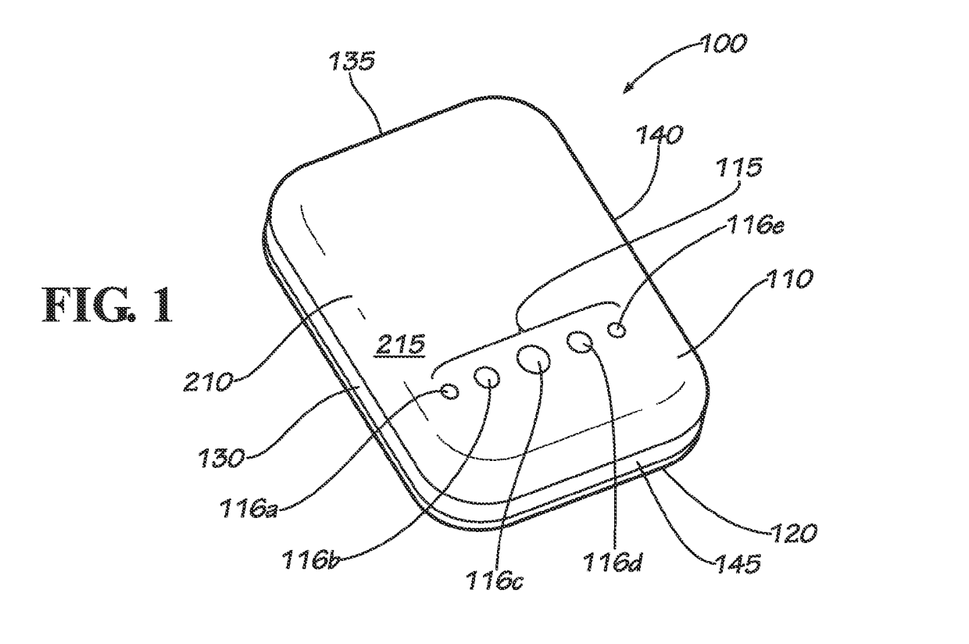
FIG. 1 is a perspective view of a safety indicator in accord with one embodiment of the current disclosure.

Disclosed is a human safety indicator for measuring and alerting a user's temperature. FIG. 1 displays a safety indicator 100. In various embodiments, the safety indicator 100 is attached to the inside of a user's hat, helmet, headband, or other headwear to provide a measurement of body temperature of the user. In other embodiments, the safety indicator 100 may be placed in contact with other body parts or otherwise in a position to measure the temperature of the user. The safety indicator 100 includes a front 110 and a back 120. The front 110 includes a temperature aperture 115 that is five holes 116a,b,c,d,e in the current embodiment, although other embodiments may include other shapes or combinations of temperature aperture 115 styles. As can be seen in the view of FIG. 1, the safety indicator 100 is generally rectangular in the current embodiment, although other embodiments may include other shapes. The front 110 includes a left side 130, a top side 135, a right side 140, a bottom side 145, an outside 210, and an inside 220 (not shown). An outside surface 215 is also shown. All references to "left" and "right" in this disclosure refer to the left and right directions when viewing the front 110 from the outside 210 with the top side 135 up and the bottom side 145 down. The front 110 has a cambered profile.

Figure 2:
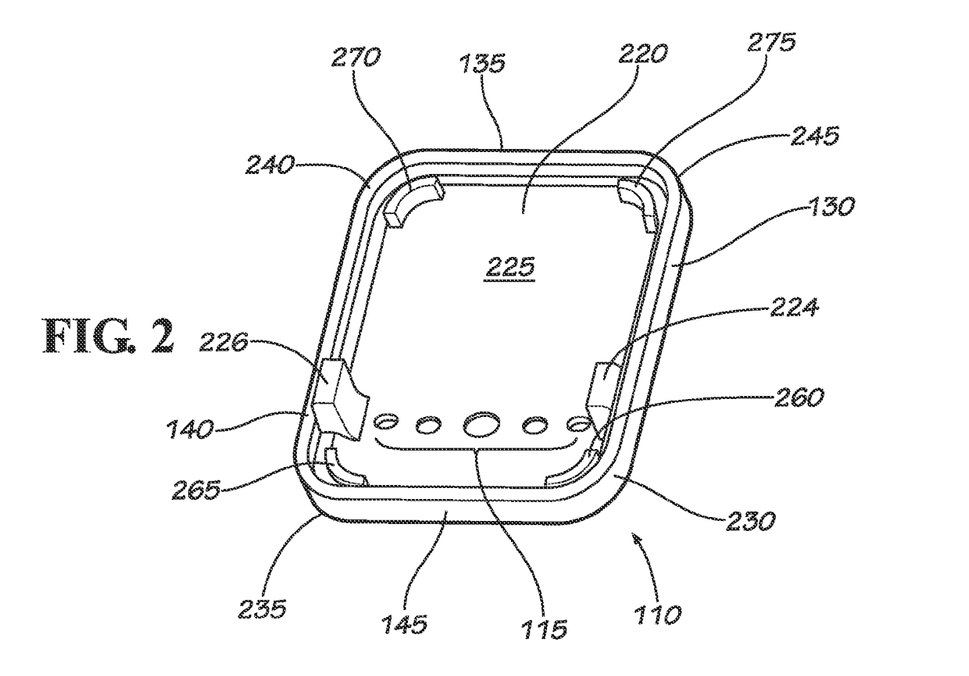
FIG. 2 is a perspective view of an inside of a front of the safety indicator of FIG. 1.

FIG. 2 displays the front 110 from an inside view. The inside 220 includes temperature probe holders 224,226. Rounded corners 230,235,240,245 connect the sides 130, 135,140,145. An inside surface 225 is shown. Four shoulders 260,265,270,275 extend from the inside surface 225. A temperature probe (not shown) is positioned between the temperature probe holders 224,226 in the current embodiment. In the current embodiment, the temperature probe is a metal tape. The metal tape temperature probe may be aluminum or copper in various embodiments. Other materials may be used in other embodiments as well. In various embodiments, other temperature probes may be used, including thermocouples, thermistors, and mercury thermometers, among others. In the current embodiment, the metal tape temperature probe is placed proximate the temperature aperture 115. In various embodiments, the front 110 or the back 120 may be made of metal, and one or both of the front 110 or the back 120 may serve as the temperature probe.

Figure 3:
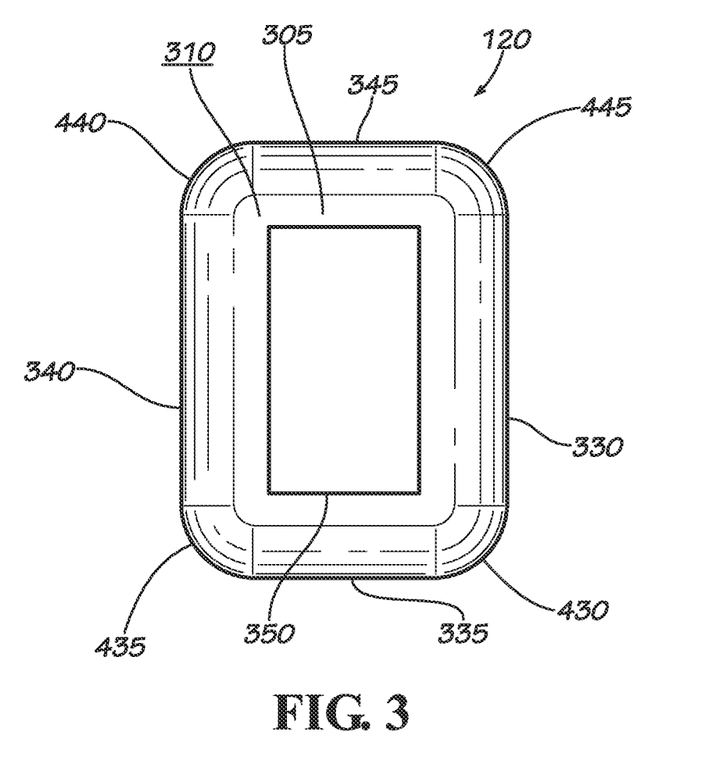
FIG. 3 is an outer side view a back of the safety indicator of FIG. 1.

FIG. 3 shows an outside view of the back 120. The back 120 includes an outside 305 and an inside (not shown). An outside surface 310 is shown on the outside 305. The back 120 includes a left side 330, a top side 335, a right side 340, a bottom side 345, and an inside 320 (not shown). Rounded corners 430,435,440,445 connect the sides 330,335,340, 345. The back 120 defines a contact hole 350 that is rectangular in shape in the current embodiment, although other shape contact holes may be used. In some embodiments, no contact hole is needed. Each of the sides 330, 335,340,345 and the corners 430,435,440,445 are filleted in the current embodiment. In various embodiments, the sides 330,335,340,345 and the corners 430,435,440,445 may be various shapes.

Figure 4:
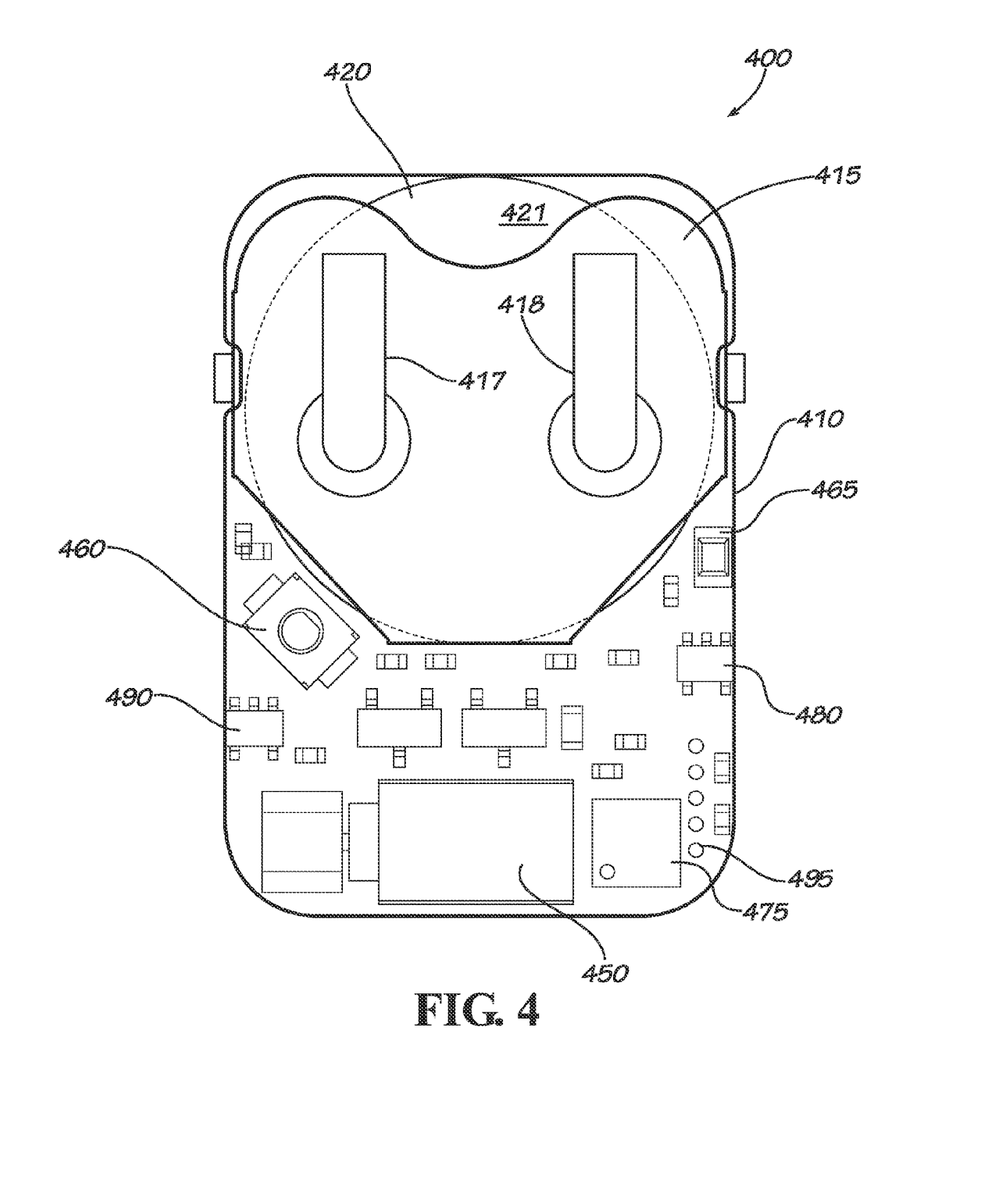
FIG. 4 is a back side view of a PCB assembly of the safety indicator of FIG. 1.

The safety indicator 100 includes a printed circuit board assembly 400 (PCB assembly) as seen in FIG. 4. The PCB assembly 400 includes a printed circuit board (PCB) 410 and a battery 420. A battery plate 415 holds the battery 420 in electrical contact with the PCB 410. The battery plate 415 includes two metal contacts 417,418 that contact the top surface 421 of the battery 420, which is the positive side of the battery 420 in the current embodiment. A portal 495 will be discussed later with reference to FIG. 13.

The PCB assembly 400 includes an alert indicator 450 and a use detector 460. In the current embodiment, the use detector 460 is a pressure sensor. The use detector 460 pressure sensor of the current embodiment is a button that may be pushed in order to detect use of the safety indicator 100. Pressure is applied to the use detector 460 pressure sensor by a button. Although the use detector 460 pressure sensor is shown on one side of the PCB 410, it may be in other places in various embodiments, including other physical locations on the PCB 410 or on the other side of the PCB 410. In other embodiments, the use detector 460 may be another type of device sufficient to determine whether the device is in use; in various embodiments, a photoelectric sensor or ambient light sensor may be used; in various embodiments, an ambient temperature sensor may be used to determine when there is a difference between the ambient temperature and the sensed temperature. In various embodiments, the temperature probe may be used as a conductivity loop to function as the use detector 460 based on electrical capacitance of touch. In various embodiments, the front 110 and back 120 may be made of conductive material, for which the front 110 and back 120 may serve as a conductivity loop to function as the use detector 460. If a conductivity loop is used, a pressure sensor may not be necessary or may be included as a redundancy. In various embodiments, multiple sensor types may be combined together to provide redundancy for the use detector 460. In the current embodiment, a use detector 465 is included to be a redundancy to use detector 460. The use detector 465 in the current embodiment is an ambient light sensor or photoelectric sensor. As such, the safety indicator 100 of the current embodiment includes two methods of determining when the safety indicator 100 is in use. In various embodiments, the use detector 460 may be activated by the flexure of the casing, particularly of the back. In various embodiments, the first activation of any use detector 460,465 may provide the activation of the safety indicator 100.

In the current embodiment, the alert indicator 450 is a vibration motor. In various embodiments, the alert indicator 450 may be other types of indicators, for example, a speaker, a light, temperature-sensitive color-shifting material, or a wireless signal among other types of indicators. Moreover, there may be various types of indicators for each method. For example, an alert indicator 450 vibration motor may be a DC motor, a stepper motor, a solenoid, or any other system configured to provide vibration through electromotive force. Similarly, an alert indicator 450 light may be an incandescent light, an LED, or a display, among others embodiments.

The PCB assembly 400 also includes two temperature sensors 480,490. The two temperature sensors are implemented for redundancy to ensure accuracy of the measured temperature. In various embodiments, one temperature sensor may be used. In various other embodiments, more than two temperature sensors may be used. In variations of the current system, the temperature sensors may be altered or combined with additional sensors to sense other human functions including blood pressure, heart rate, and caloric data, among others. A microcontroller 475 is included in the PCB assembly 400. In the current embodiment, the microcontroller 475 is a Microchip PIC, although other microcontrollers 475 may be used in various embodiments, including ICs, other microchip, microprocessors, and other electronic circuitry, among others.

It should be noted that other features of the PCB assembly 400 are shown but not referenced. These features should not be considered limiting on the disclosure but are provided for a full disclosure. Such features may be referenced in later documents flowing from this disclosure; however, no single feature should be considered limiting on the breadth or scope of claimable disclosure.

Figure 5:
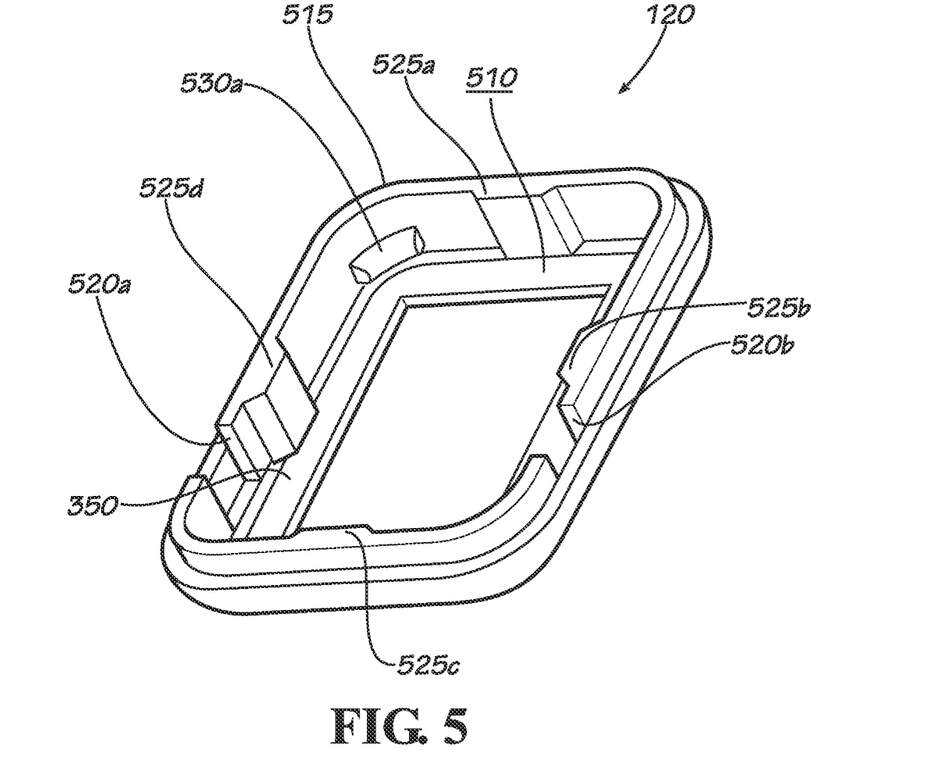
FIG. 5 is an inside perspective view of the back of FIG. 3.
Figure 12:
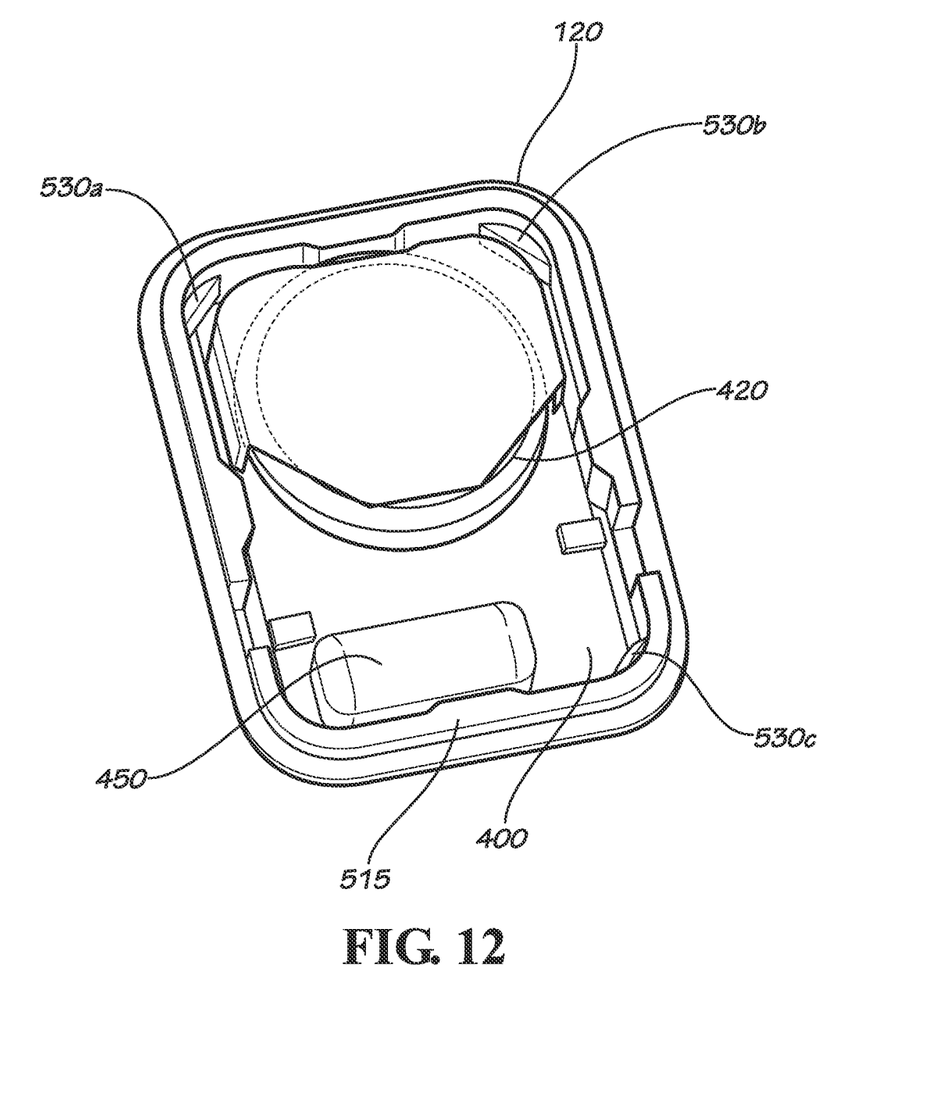
FIG. 12 is an inside perspective view of the PCB assembly of FIG. 4 together with the back of FIG. 3.

FIG. 5 shows an inside perspective view of the back 120. The inside surface 510 of the back includes multiple features. A weld shoulder 515 follows the perimeter of the back 120 providing a weld interface with the front 110. The weld shoulder 515 includes two holder pockets 520*a,b* so that the temperature probe holders 224,226 may be fit into the back without interference. The back 120 includes several locating bosses 525*a,b,c,d* located on the inside surface 510 at each side of the weld shoulder 515 to locate the PCB 410 and, thereby, the PCB assembly 400. Also, locking tabs 530*a* (530*b,c,d* not shown) are located at the corners of the inside of the weld shoulder 515 to hold the corners of the PCB 410. The interaction of the PCB assembly 400 and the back 120 is shown in FIG. 12.

Figure 6:
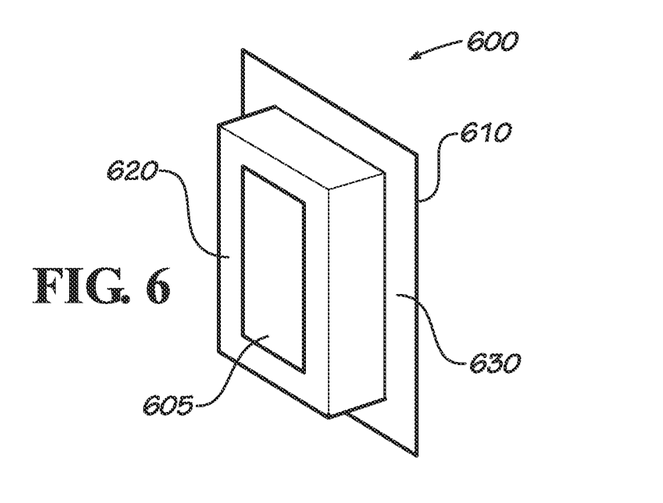
FIG. 6 is a perspective view of a pressure button assembly of the safety indicator of FIG. 1.

FIG. 6 shows a pressure button assembly 600 which includes a pressure button 610 and a connection pad 605. In the current embodiment, the connection pad 605 is a glue pad. In other embodiments, the connection pad 605 may be other affixing means, such as Velcro, variations of Velcro, tape, magnets, or, among others, mechanical affixing means such as mechanical winged tabs, clips, fingers, and other mechanical affixing means. The pressure button 610 has a button portion 620 and a flange portion 630. The button portion 620 is sized so that it may occupy the space provided by the contact hole 350. The flange portion 630 is sized larger than the contact hole 350 so that it may retain the pressure button 610 inside the safety indicator 100.

Figure 7:
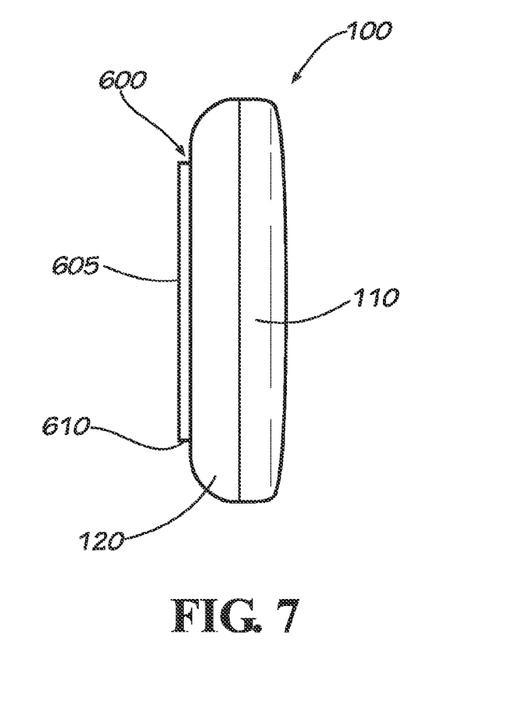
FIG. 7 is an outer side view of the safety indicator of FIG. 1.

As seen in FIG. 7, when the safety indicator 100 is assembled, the front 110 and the back 120 are placed together. The front 110 and the back 120 are ABS plastic in the current embodiment, although other material choices may be used in other embodiments, including silicone, metal, other plastics, wood, resin, epoxy, foam, rubber, and other materials. In the current embodiment, the front 110 and back 120 are plastic welded to prevent the introduction of contaminants at the border, such as water or sweat. The metal tape temperature probe (not shown) is attached to the inside of the front 110. The PCB assembly 400 is placed such that the temperature probe is between the front 110 and PCB assembly 400. The pressure button assembly 600 is then placed between the PCB assembly 400 and the back 120, wherein the back 120 and front 110 together enclose the temperature probe, the PCB assembly 400, and the pressure button assembly 600. While the pressure button assembly 600 is captured, only the flange portion 630 is restricted, as the button portion 620 and connection pad 605 protrude through the contact hole 350, as shown. The pressure button assembly 600 is aligned such that any pressure on the pressure button assembly 600 will push the pressure button assembly 600 into the use detector 460, which is a pressure sensor in the current embodiment. When the use detector 460 pressure sensor is pressed, it senses that pressure has been applied and thereby that the safety indicator 100 is ready for use. In the current embodiment, the second use detector 465 is an ambient light sensor. It detects use whenever the light sensor is covered or in the shadows. In the current embodiment, both are activated to allow the safety indicator 100 to begin measuring the user's temperature. In various other embodiments, one use detector 460, 465 may be used and may be of any variety of sensor. In various other embodiments, no use detector 460,465 will be included, and the safety indicator 100 will be continuously on.

In various embodiments, functions of the use detector 460,465 are performed through electronic switching. For example, in one embodiment, use detection occurs based on the temperature that is sensed. The safety indicator 100 remains in sleep state so long as the sensed temperature remains below a "human condition," which occurs at human body temperature (98.6 degrees Fahrenheit). The human condition that is sensed may be adjusted for heat conductivity of the materials of the safety indicator 100. In the current embodiment, the adjustment is approximately three degrees Fahrenheit, so the human condition occurs at a sensed temperature of about 95 degrees Fahrenheit as correlated to a human body temperature of about 98.6 degrees Fahrenheit. Once the safety indicator 100 determines that it is in the human condition, it awakens from sleep state to operation, wherein it provides an indication that it is awake—in the current embodiment, one vibration, although a different number of vibrations may be used in other embodiments as well as other indication methods including lights, sounds, and other sensations, among other indication methods. The safety indicator 100 remains in operation until the sensed temperature falls below 93 degrees Fahrenheit, at which point the safety indicator 100 determines that it is no longer in the human condition and likely not in use by a human.

Once assembled, the safety indicator 100 is prepared for use. For control of battery life, the safety indicator 100 is packed in a sleep mode and is not using substantial battery power. As stated previously, the safety indicator 100 of the current embodiment is intended to be affixed to the user's hat, helmet, headband, or other headwear to provide a measurement of body temperature of the user. The connection pad 605 in the current embodiment is a glue pad, which is supplied to the user with a backing. Upon receiving the safety indicator 100, the user removes the backing and presses the connection pad 605 against the inside of the user's headwear in a location to contact the user's temple. When the user applies pressure to the safety indicator 100 to seat the connection pad 605 glue against the headwear, the use detector 460 is activated by the pressure. This activation is the first activation of the safety indicator 100 and begins an internal clock (not shown). If no use detector 460 pressure sensor is included, the function can be performed by other types use detectors. One of skill in the art will understand some changes in methodology may need to be implemented in order to support changes in the type of use detector implemented.

In the current embodiment, when the use detectors 460, 465 are not activated, the safety indicator 100 is in sleep mode and is not measuring temperature. The sleep mode uses little electrical energy of the battery 420. However, when the use detectors 460,465 are activated by pressure and light, respectively, the safety indicator 100 is in operation, actively measuring temperature and using substantially more electrical energy of the battery 420. When one of the use detectors 460,465 becomes inactive, the safety indicator 100 returns to sleep mode until it may be activated again.

It is understood that the battery life of the safety indicator 100 is unknown and depends greatly on the amount of use in operation. The user may be exposed, thereby, to an unsafe condition if he is actively using a safety indicator 100 with a weak battery 420 or with poor battery life. As such, it is a safety feature of the current embodiment to deplete any remaining electrical energy stored in the battery 420 at the expiration of one year from the activation of the safety indicator 100. When the internal clock reaches one year, the safety indicator 100 permanently activates to operation and does not return to sleep mode. The battery 420 depletes, and the safety indicator 100 should be disposed by the user. In the current embodiment, the alert indicator 450 activates to deplete the battery 420.

In operation, the safety indicator 100 operates by measuring temperature using the temperature probe. The temperature probe measures temperature at the user's temple when the safety indicator 100 is in contact or proximate to the user's temple. A user temperature is gained using the average (mean) value of the two temperature sensors 480, 490, which are measuring from the same temperature probe. The averaging to determine user temperature provides validation against false readings, as the redundancy ensures that correct values will be determined.

The safety indicator 100 will include a maximum user temperature and a minimum user temperature. The maximum user temperature and minimum user temperature are programmable. Moreover, the user temperature that is sensed is a skin-level temperature; as previously described, the skin-level temperature is adjusted to correlate for the difference between skin temperature in the temporal region and core body temperature. The adjustment needed is approximately 3.2 degrees Fahrenheit. Should the user temperature exceed the maximum user temperature or fall below the minimum user temperature, the alert indicator 450 will activate, identifying a problem to the user. In the current embodiment, the activation of the alert indicator 450 is by means of a vibration motor turning on, thereby causing the safety indicator 100 to vibrate. The user feels the vibration of the safety indicator 100, thereby noticing that his or her temperature has exceeded the maximum user temperature or fallen below the minimum user temperature, for which the user should seek aid. In some embodiments, the maximum user temperature is 102.5 degrees Fahrenheit.

In some embodiments, safety indicators 100 may be integrated into a network for reporting such temperature data to a central location, to a wireless computer, or otherwise to a network. The current embodiment does not report such data to a central location but instead relies on the user to self-report his or her temperature safety.

The method as described above is shown in FIG. 8. Initial activation of the use detector 460 activates the safety indicator 100 as shown in step 805. Immediately following activation, the internal clock starts as in step 810, from which one year will be determined. Sleep mode 815 is indicated by the dotted line box called out in the flow diagram. The sleep mode 815 includes first step 820, wherein the internal clock is checked to ensure that less than one year has passed since activation, followed by step 825, wherein both use detectors 460,465 are checked to determine whether to remove the safety indicator 100 from sleep mode 815. If both use detectors 460,465 are activated, the safety indicator 100 goes into operation 830 as denoted by the dotted line box.

Figure 8:
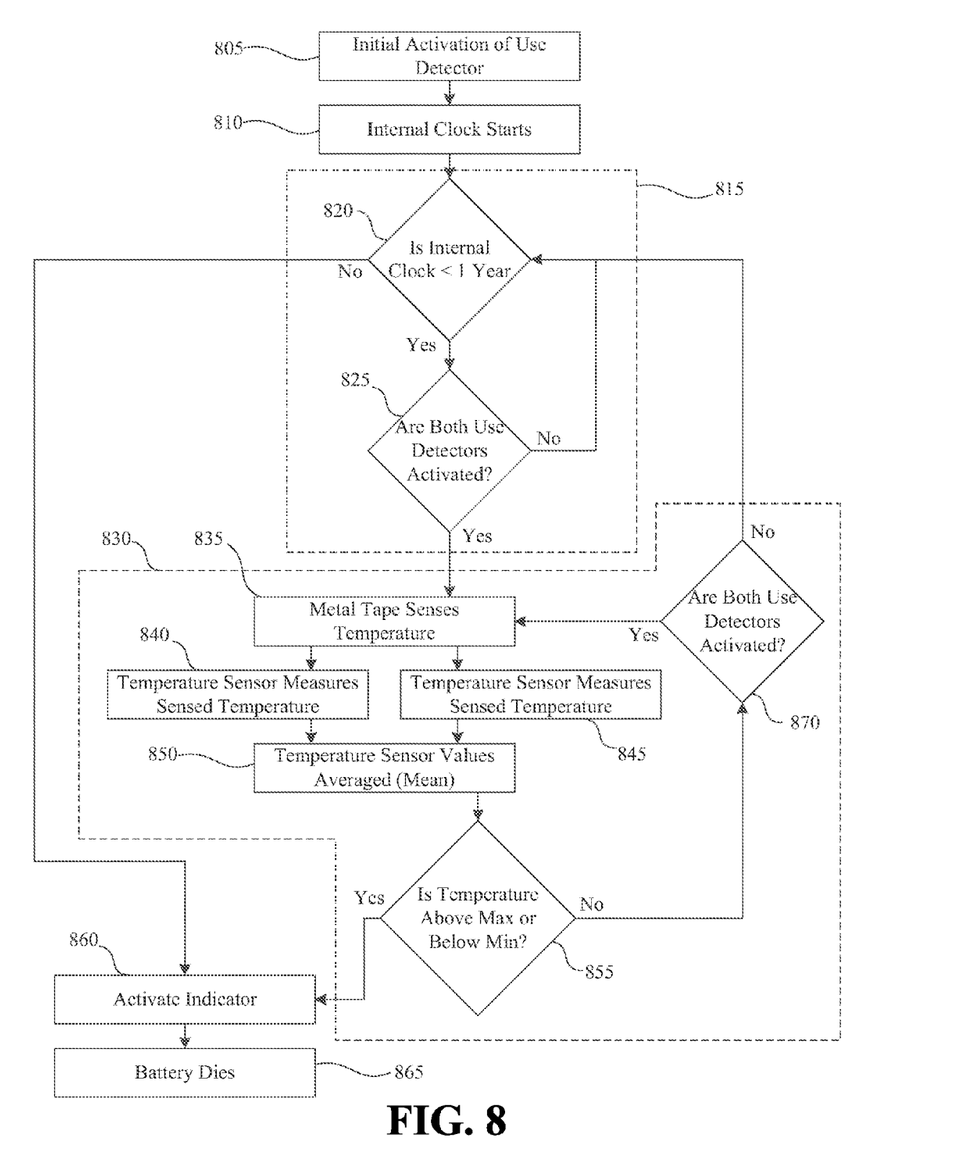
FIG. 8 is a flow diagram illustrating a method in accord with one embodiment of the current disclosure.

In operation 830, the user's body heat is transmitted into the temperature probe as indicated in step 835. The temperature of the temperature probe is measured by the temperature sensors 480,490 in parallel as indicated in steps 840 and 845. The measured values of the temperature sensors 480,490 are averaged as in step 850 to determine the user temperature. The user temperature is compared to the maximum and/or the minimum allowable user temperatures as shown in step 855.

Regarding step 855, in most cases, the user temperature will fall within the allowable temperature range. If so, the flow diagram proceeds to reevaluate whether both use detectors 460,465 remain activated, as shown in step 870. If both use detectors 460,465 are still activated, the flow diagram loops to step 835. If one or more of the use detectors 460,465 is not activated, the flow diagram leaves operation 830 and returns to step 820 in sleep mode 815.

On the other hand, if step 855 determines that the user temperature is outside of the allowable range, the flow diagram proceeds to activate the alert indicator 450 as shown in step 860. In the current embodiment, the alert indicator 450 remains active until the battery 420 loses all electrical charge and dies, as indicated by step 865. In various embodiments, the alert indicator 450 may be permitted to deactivate if the user temperature returns to the allowable range. The alert indicator 450 may include a series of vibrations in various embodiments, of which one example can be seen in FIG. 11.

As described previously, the electrical energy stored in the battery 420 is depleted at the expiration of one year from the activation of the safety indicator 100. As shown by step 820, reading of the internal clock is performed many times over the life of the safety indicator 100. If the internal clock indicates that the safety indicator 100 has been active for over one year, step 820 bypasses all remaining steps in the flow diagram, proceeding to activate the alert indicator 450 as shown in step 860 until the battery 420 dies as indicated by step 865. This battery 420 depletion process will occur regardless of whether the user temperature is within or is outside of the allowable range. One of skill in the art will understand variations on this methodology will be supported by variations in flow of the method and will depend on which hardware is implemented into each embodiment safety indicator 100.

Figure 9:
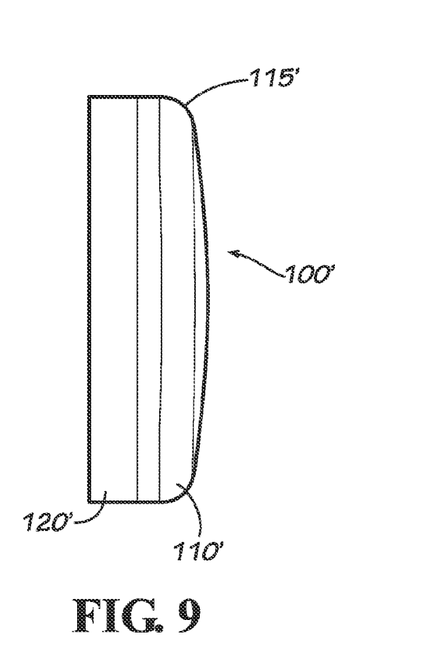
FIG. 9 is an outer side view of a safety indicator in accord with one embodiment of the current disclosure.

FIG. 9 displays another embodiment of a safety indicator 100'. As can be seen, the safety indicator 100' includes a front 110' and a back 120'. The front 110' is cambered much like the front 110 but includes rounded edges 115'. The back 120' does not include any rounded edges as does the back 120.

Figure 10:
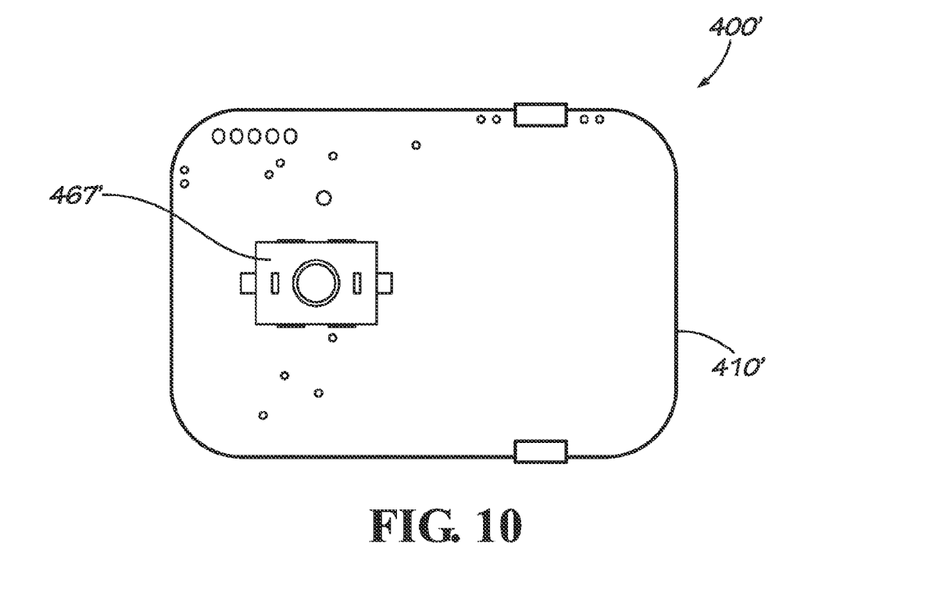
FIG. 10 is a front side view of a PCB assembly in accord with one embodiment of the current disclosure.

FIG. 10 displays another embodiment of a PCB assembly 400'. In the current embodiment, the PCB assembly 400' has a use detector 467' located on a side of the PCB 410' opposite to the other use detectors 460,465. The use detector 467' is a pressure sensor in the current embodiment. The use detector 467' provides a second-level redundancy in the current embodiment to ensure that that safety indicator 100 is not activated unless it is in use by a user.

Figure 11:
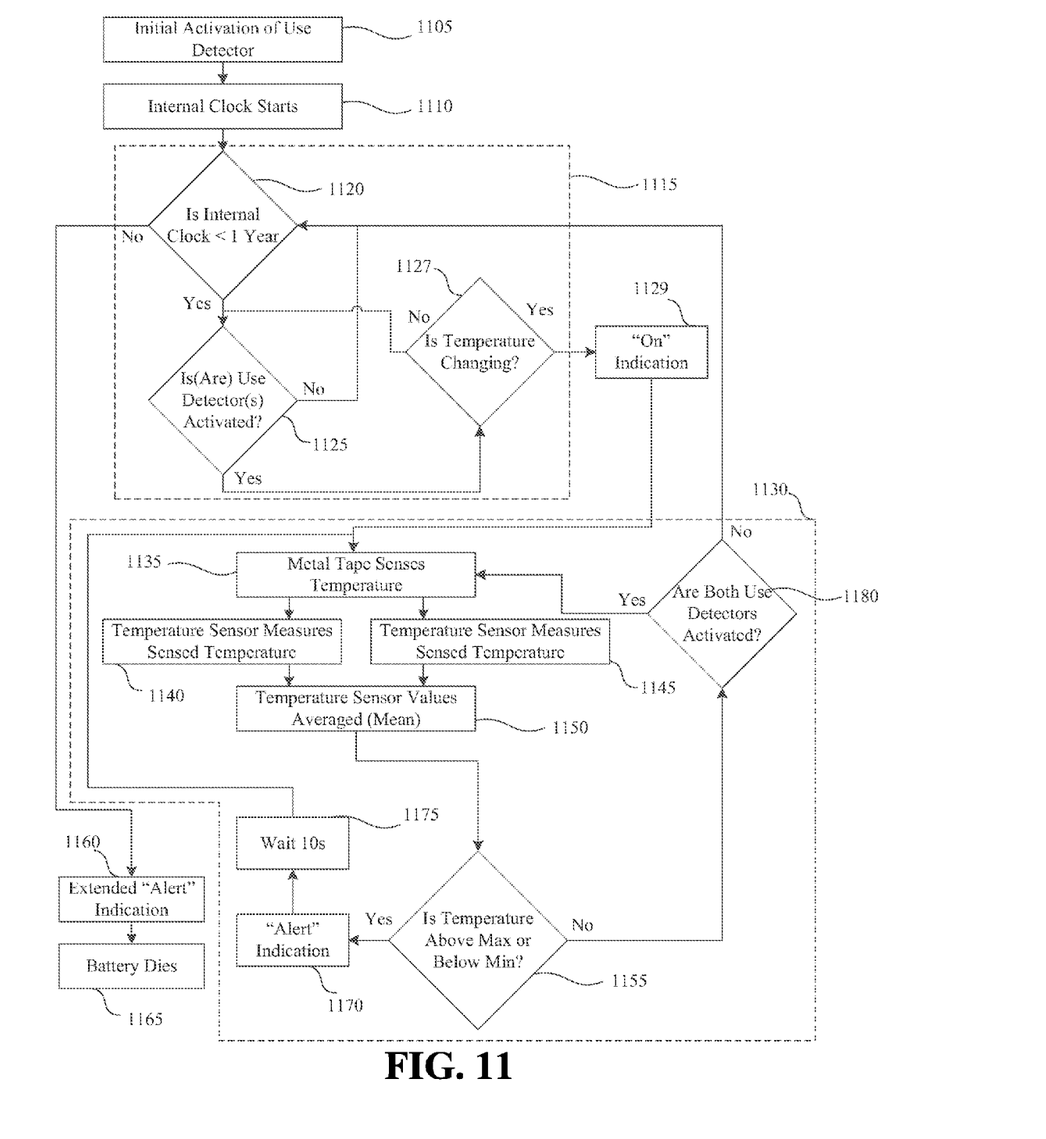
FIG. 11 is a flow diagram illustrating a method in accord with one embodiment of the current disclosure.

Another embodiment of a method is described in FIG. 11. The method begins similarly to the method of FIG. 8, wherein the initial action of the use detector 460 as shown in step 1105 causes the internal clock to start as shown in step 1110 followed by testing whether the internal clock is less than one year as indicated in step 1120 and then determining whether both use detectors are activated in step 1125. However, sleep mode 1115 differs from sleep mode 815 in that it includes a step 1127 to check whether the temperature is changing. If not, the method stays in sleep mode 1115 as indicated. If so, the method proceeds to step 1129 wherein an "on indication" is given to alert the user that the safety indicator 100 is going into operation 1130. In the current embodiment, the on indication is a single vibration produced by the alert indicator 450 vibration motor.

When the safety indicator 100 is in operation 1130, the temperature probe receives heat from the user's body as shown by step 1135. In steps 1140 and 1145, the temperature sensors 480,490 measure heat sensed from the temperature probe. The values of the temperature sensors 480,490 are averaged in step 1150 to achieve a user temperature, and the user temperature is compared to the maximum and minimum allowable user temperature in step 1155.

As with the method of FIG. 8, in most scenarios, the user temperature will be within the allowable range when compared by step 1155. In such a case, the flow diagram proceeds to step 1180 to determine if the use detectors 460,465 are still activated. If so, the flow diagram loops to step 1135. If not, the flow diagram returns to sleep mode 1115 at step 1120.

However, if the user temperature is out of the allowable range as determined by step 1155, an "alert indication" is produced by the alert indicator 450 as shown in step 1170. In the current embodiment, the alert indication is four consecutive vibrations. Following the alert indication, the flow diagram proceeds to step 1175 to wait ten seconds before restarting the method of operation and, potentially, re-alerting the user if his or her temperature remains outside of the allowable range. In various embodiments, the waiting periods may be longer or shorter. Following step 1175, the flow diagram returns to step 1135.

In another embodiment, the method of FIG. 11 may be modified to produce one alert indication when the user temperature falls outside of the acceptable range but to wait 45 seconds before re-alerting the user so that the user temperature may fall back within the acceptable range. If the user temperature does not fall back within the acceptable range, the alert indications continue on a 10-second interval as described above.

As with the method of FIG. 8, an added safety feature allows the battery 420 to be depleted upon the expiration of one year. If the internal clock is greater than one year as compared in step 1120, the flow diagram proceeds to an "extended alert indication" as shown in step 1160 wherein the alert indication continues for an extended period of time until the battery 420 is exhausted of electrical charge, as shown in step 1165.

In some embodiments, the safety indicator 100 may be configured to disregard temperature readings in excess of 105.0 degrees Fahrenheit as a non-human temperature reading. This reading is termed a lockout threshold. In some embodiments, the temperature sensors 480,490 may be programmed to calibrate for a minimum of 60 seconds before triggering an alert.

In some embodiments, a sensed temperature that exceeds the lockout threshold may decrease when the safety indicator 100 comes in contact with the user. For example, if a safety indicator 100 is exposed to solar radiation for an extended amount of time, the sensed temperature may exceed 105.0 degrees Fahrenheit. When the user applies the safety indicator 100, the sensed temperature will decrease because the user's temple will be at a temperature below 105.0 degrees Fahrenheit. In such cases, the safety indicator 100 may be configured to disregard temperature readings in excess of 102.5 degrees Fahrenheit—those that would normally trigger an alert—until the user temperature is sensed below 102.5 degrees Fahrenheit.

In other embodiments, the safety indicator 100 will be configured to delay any alert for 60 seconds when the safety indicator 100 leaves the lockout threshold, allowing the safety indicator 100 time to measure a true user temperature.

As shown in FIG. 12, the PCB assembly 400 is inserted into the back 120 so that corners of the PCB assembly 400 are locked behind the locking tabs 530*a,b,c* (530*d* not shown). The placement of the battery 420 and the alert indicator 450 can be seen with respect to the back 120. In the current embodiment, the alert indicator 450 includes a protective cover. Other features of the PCB assembly 400 are obstructed from view in the current embodiment.

Figure 13:
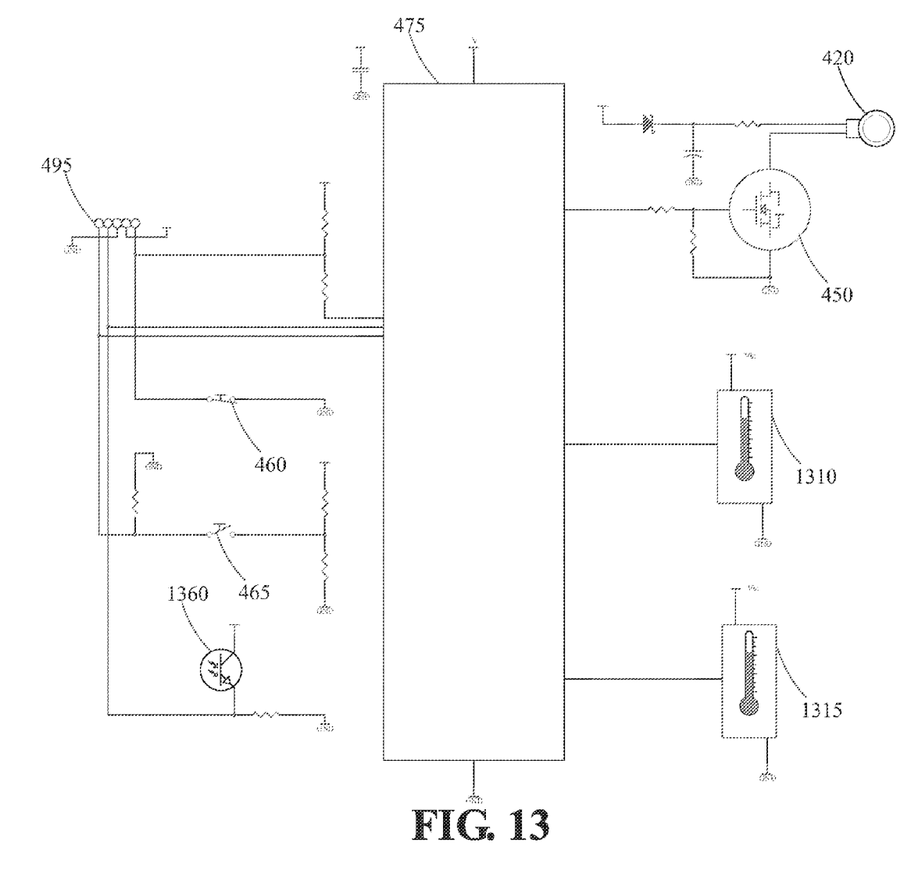
FIG. 13 is a schematic a safety indicator in accord with one embodiment of the current disclosure.

FIG. 13 shows a schematic of one embodiment of a safety indicator 1000. The use detector 460 is connected to the temperature sensors 480,490. The alert indicator 450 vibration motor is connected to the circuit as is the battery 420. The safety indicator 1000 of the current embodiment includes two use detectors 460,465 that are pressure sensors as well as a use detector 1360 that is an ambient light sensor. In the current embodiment, all use detectors 460,465,1360 must be activated to remove the safety indicator 1000 from sleep mode and place it in operation. The use detectors 460,465,1360 are connected to pins of the microcontroller 475. Temperature sensors 1310,1315 are connected to pins of the microcontroller 475. A pin of the microcontroller 475 is connected to the alert indicator 450 vibration motor. Although the control circuitry is powered by the battery 420, the alert indicator 450 is shown with a direct connection to the battery 420. A portal 1395 is also shown as included to allow connection for testing and for programming, although such portal 1395 is not available to the user in the current embodiment. Other circuitry and features are shown but not referenced or are not shown. However, supporting circuitry would be understood by one of skill in the art.

Figure 14:
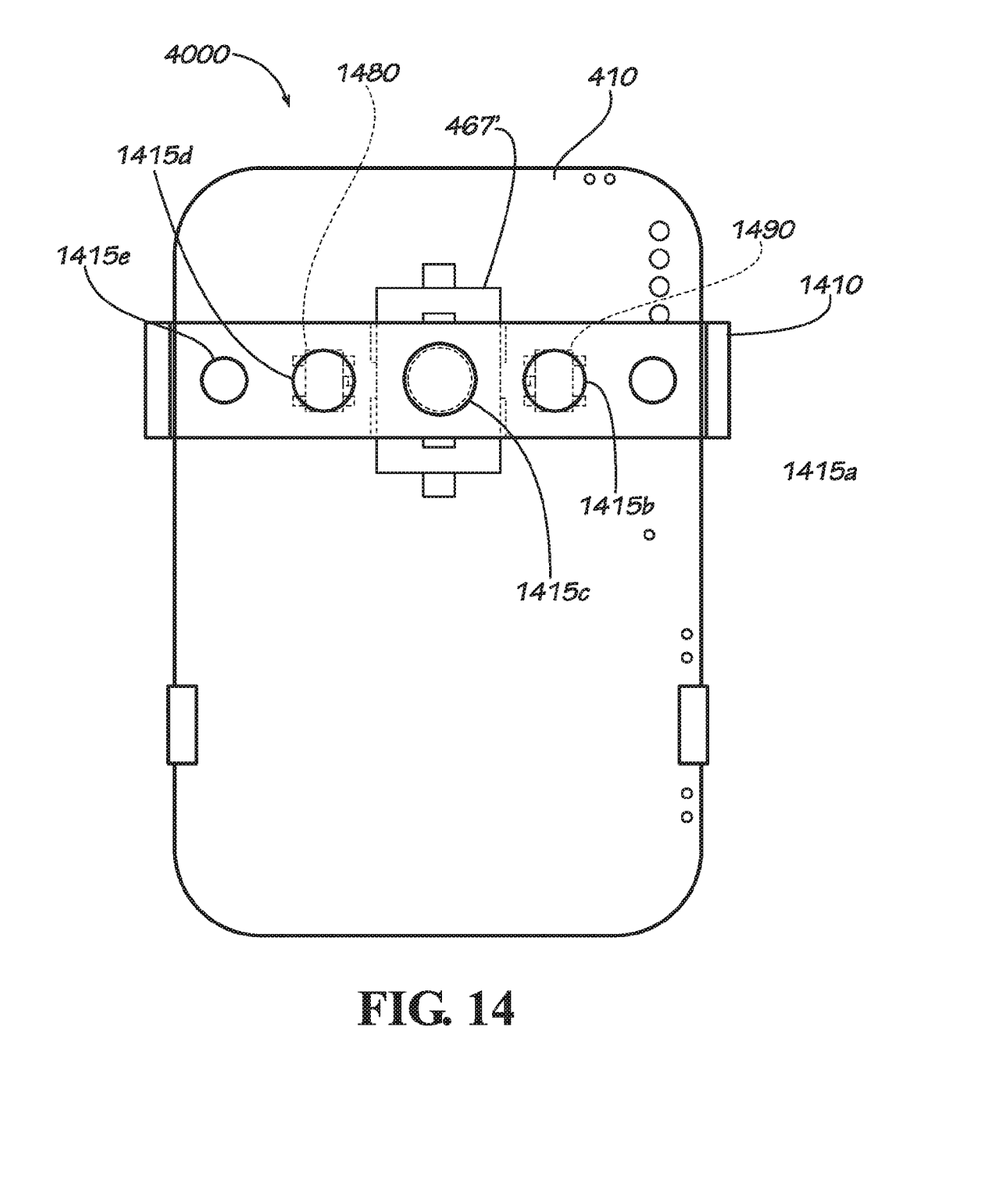
FIG. 14 is a front side view of a PCB assembly in accord with one embodiment of the current disclosure.

Another embodiment of a PCB assembly 4000 is shown in FIG. 14. The PCB assembly 4000 of the current embodiment is designed to interface with a specialized temperature probe 1410. In other embodiments of the safety indicator 100, the temperature probe is a flat metal tape. In the current embodiment, the temperature probe 1410 includes five dimples 1415*a,b,c,d,e*. The dimples 1415*a,b,c,d,e* interface with the five holes 116*a,b,c,d,e* that are the temperature aperture 115. The dimples 1415*a,b,c,d,e* protrude up from the temperature probe 1410 and into the five holes 116*a,b, c,d,e* so that the temperature probe 1410 makes more direct contact with the user's skin than with a flat tape temperature probe. Also, in the embodiment of FIG. 14, two additional temperature sensors 1480,1490 are mounted to the PCB 410. The location of the temperature sensors 1480,1490 allows them to make a quicker reading of temperature coming through the temperature probe 1410 because heat need not travel all the way to the other side of the PCB 410 to reach temperature sensors 480,490. In some embodiments, the temperature sensors 1480,1490 will be redundant to temperature sensors 480,490. In various embodiments, any number or placement of temperature sensors 480,490,1480, 1490 may be used. It can also be seen that use detector 467' is included in the current embodiment, wherein it is placed under the temperature probe 1410 so that it interfaces with dimple 1415*c*. The use detector 467' may be placed under any dimple 1415*a,b,c,d,e*, under other parts of the temperature probe 1410, at other locations on the PCB 410, or may be omitted in various embodiments.

One feature of the safety indicator 100 is that, in the current embodiment, it does not require systems, electronic links, wireless connections, or infrastructure to implement—although such features may be added in other embodiments. Instead, in the current embodiment, it is the user's responsibility to acquire the safety indicator 100, to place the safety indicator 100 in the user's headwear, to recognize overheating alarms of the safety indicator 100, and to report overheating to a supervisor, a coach, or another individual, or to remove himself or herself from the activity causing overheating. The effect of this is to shift potential liability away from supervisors and or coaches in the organizational setting.

Additionally, because the safety indicator 100 is designed for individual use, the cost is minimal as compared to comparable systems and/or methods of monitoring outdoor exposure to heating. As such, individuals may obtain and use the safety indicator 100 for any activity, including those for which no organization is required such as jogging, cross-training, cycling, gardening, and all other outdoor or otherwise heat-intensive activities. Moreover, the safety indicator 100 does not require reporting apparatus or infrastructure, so an individual need not purchase extra equipment to implement it. The safety indicator 100 is ready for use in a user's headwear—or otherwise as implemented in various embodiments—as soon as its packaging is opened.

It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. Unless stated otherwise, it should not be assumed that multiple features, embodiments, solutions, or elements address the same or related problems or needs.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

What is claimed is:

1. A human safety system comprising:
   a circuit including at least one power source;
   an internal clock configured to deplete the at least one power source after a first predetermined time period;
   a temperature probe in communication with the circuit and configured to measure a user temperature;
   at least one use detector in communication with the circuit, the at least one use detector adapted to:
     detect if the human safety system is in use;
     activate the human safety system when the temperature probe detects the user temperature is changing; and
     start the internal clock after a first activation of the human safety system; and
   an alert indicator in communication with the circuit, the alert indicator configured to provide indication when the human safety system is activated by the at least one use detector and:
     the user temperature is above a maximum user temperature but is below a maximum human condition temperature;
     the user temperature is below a minimum user temperature but above a minimum human condition temperature; or
     the internal clock exceeds the first predetermined time period;
   wherein the maximum user temperature is less than the maximum human condition temperature,
   wherein the minimum user temperature is greater than the minimum human condition temperature and less than the maximum user temperature, and
   wherein the at least one use detector is adapted to deactivate the human safety system when the user temperature is above the maximum human condition temperature for a second predetermined time period or the user temperature is below the minimum human condition temperature for a third predetermined time period.

2. The human safety system of claim 1, wherein the human safety system is not in operation subsequent to the first activation until at least one use detector is activated.

3. The human safety system of claim 2, wherein the human safety system is not in operation subsequent to the first activation until more than one use detector is activated.

4. The human safety system of claim 2, wherein the temperature probe is a thermocouple.

5. The human safety system of claim 2, wherein the temperature probe is metal.

6. The human safety system of claim 5, wherein at least one use detector is a pressure sensor.

7. The human safety system of claim 5, wherein at least one use detector is a light sensor.

8. The human safety system of claim 5, wherein the temperature probe is a metal enclosure of the human safety system.

9. The human safety system of claim 5, wherein the temperature probe is a metal tape.

10. The human safety system of claim 5, wherein at least one use detector is activated by the temperature probe reaching a human condition.

11. The human safety system of claim 5, wherein a temperature for activation of the use detector is measured at the temperature probe.

12. The human safety system of claim 5, wherein the alert indicator includes an audio transducer.

13. The human safety system of claim 5, wherein the alert indicator includes a light.

14. The human safety system of claim 5, wherein the alert indicator is a vibration motor.

15. A method of operating a human safety indicator, the method comprising:
   receiving a maximum user temperature and a minimum user temperature with a microcontroller, wherein the maximum user temperature is less than a maximum human condition temperature and wherein the minimum user temperature is greater than a minimum human condition temperature and less than the maximum user temperature;
   sensing with the microcontroller at least one user temperature using a temperature probe;
   determining with the microcontroller whether at least one use detector is active and in use;
   determining with the microcontroller whether the at least one sensed user temperature is changing;
   activating a safety indicator upon determining with the microcontroller that the at least one use detector is active and the at least one sensed user temperature is changing;
   starting an internal clock with the microcontroller after a first activation of the safety indicator, the internal clock configured to deplete a power source of the human safety indicator after a first predetermined time period;
   determining with the microcontroller whether the at least one sensed user temperature is less than a maximum user temperature and greater than a minimum user temperature;
   determining with the microcontroller whether the at least one sensed user temperature is greater than the maximum user temperature or less than a minimum user temperature;
   alerting with the microcontroller if:
     the user temperature is greater than the maximum user temperature and less than the maximum human condition temperature;
     the user temperature is less than the minimum user temperature but greater than the minimum human condition temperature; or
     the internal clock exceeds the first predetermined time period; and
   deactivating the safety indicator with the microcontroller upon determining that the at least one sensed user temperature is greater than the maximum human condition temperature for a second predetermined time period or the at least one sensed user temperature is less than the minimum human condition temperature for a third predetermined time period.

16. The method of claim 15, further comprising the step of alerting with the microcontroller if the user temperature is less than the minimum human condition temperature or greater than the maximum human condition temperature.

17. The method of claim 16, wherein the maximum user temperature is about 102.5 degrees Fahrenheit.

18. The method of claim 15, further comprising determining a user temperature based on a sensed temperature by:
   sensing temperature of at least two temperature sensors with the microcontroller; and
   determining the user temperature by averaging the sensed temperatures of the at least two temperature sensors with the microcontroller.

19. The method of claim 15, wherein the step of determining with the microcontroller whether at least one use detector is active includes determining whether the sensed temperature is within a range of a human condition.

20. The method of claim 19, wherein the human condition begins at about 98.6 degrees Fahrenheit.

21. The human safety system of claim 1, wherein the second predetermined time period is equal to the third predetermined time period.

22. The method of claim 15, wherein the second predetermined time period is equal to the third predetermined time period.

* * * * *